United States Patent [19]

Panke et al.

[11] 4,134,970

[45] Jan. 16, 1979

[54] QUATERNARY AMMONIUM COMPOUNDS AND THEIR USE IN HAIR CARE COMPOSITIONS

[75] Inventors: Hans L. Panke, Frankfurt am Main; Willi Steckelberg, Hofheim im Taunus; Jochen M. Quack, Kelkheim; Alwin Reng, Frankfurt am Main, all of Fed. Rep. of Germany

[73] Assignee: Hoechst Aktiengesellschaft, Frankfurt am Main, Fed. Rep. of Germany

[21] Appl. No.: 807,403

[22] Filed: Jun. 17, 1977

[30] Foreign Application Priority Data

Jun. 23, 1976 [DE] Fed. Rep. of Germany ....... 2628157

[51] Int. Cl.$^2$ .................. A61K 7/06; A61K 7/08; C07C 141/02; C07C 87/30
[52] U.S. Cl. ................................. 424/70; 252/547; 252/DIG. 13; 260/459 A; 260/567.6 M
[58] Field of Search .................. 260/459 A, 567.6 M; 424/70

[56] References Cited

U.S. PATENT DOCUMENTS

| | | | |
|---|---|---|---|
| 2,554,441 | 5/1951 | Cross et al. | 260/567.6 M |
| 2,918,401 | 12/1959 | Copp | 260/459 A |
| 3,155,591 | 11/1964 | Hilfer | 260/567.6 M |
| 3,424,794 | 1/1969 | Miller et al. | 260/459 A |

Primary Examiner—Joseph E. Evans
Attorney, Agent, or Firm—Connolly and Hutz

[57] ABSTRACT

Quaternary ammonium compounds of the formula I

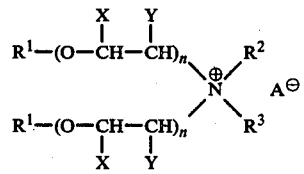

wherein $R_1$ is $C_8$–$C_{24}$ alkyl, cyclohexyl or aryl, X and Y are hydrogen or methyl, only one X or Y being methyl at the same time, n is an integer of from 1 to 20, $R^2$ and $R^3$ are lower alkyl or benzyl and A is an anion. These compounds are made by common alkylation reaction of the corresponding non-quaternized compounds. They are used as surfactants, especially in hair care compositions.

9 Claims, No Drawings

QUATERNARY AMMONIUM COMPOUNDS AND THEIR USE IN HAIR CARE COMPOSITIONS

The present invention relates to quaternary ammonium compounds, a process for preparing them and their use.

The present invention provides novel quaternary ammonium compounds of the general formula (I)

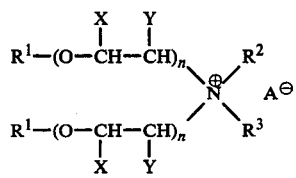

in which $R^1$ is a saturated or unsaturated alkyl radical having 8 to 24 carbon atoms, a cyclohexyl radical or an aryl radical optionally substituted by alkyl groups, X and Y stand for a hydrogen atom or a methyl radical, however, X and Y not being methyl at the same time, n is a number of 1 to b 20, $R^2$ and $R^3$ stand for an alkyl radical of 1 to 4 carbon atoms or a benzyl radical, and A represents the methosulfate ion, a chloride or bromide.

These compounds are prepared by quaternization of secondary ether amines of the general formula (II)

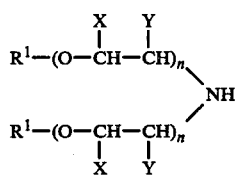

with common alkylation reagents, such as alkyl halides, alkyl sulfuric acid esters or benzyl chloride in the presence of alkali metal. In this process the reaction conditions may vary within wide limits.

The reaction is preferably carried out at an elevated temperature in the range of from 30 to 160° C in solvents, such as water, alcohols, for example, ethanol or isopropanol, aromatic hydrocarbons, such as toluene or xylene, or in polar aprotic solvents, for example, dimethylformamide, and in the presence of alkali metal, such as sodium hydroxide, sodium carbonate or sodium hydrogenocarbonate, however, it may also be carried out at room temperature or without solvent. In order to obtain uncolored products it is advantageous to carry out this reaction in the presence of an inert gas, for example, nitrogen.

The secondary ether amines of the formula (II) are obtained according to the process described in German Pat. application No. P 25 55 895.6-42 by reacting oxalkylates of the formula III

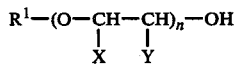

in which $R^1$, X, Y and n are defined as in formula (I) above, in the liquid phase with ammonia and hydrogen in the presence of hydrogenation-dehydrogenation catalysts, especially nickel and cobalt catalysts, with a gas rate of at least 10 l/kg of oxalkylate · h at a temperature of from 150 to 250° C and in the range of atmospheric pressure at 0.5 to 1.5 atmospheres gage, and by eliminating the reaction water with the gas stream.

The saturated and unsaturated alcohols which are at the basis of the oxyalkyl derivatives of the formula III and which form the radical $R^1$ in the compounds of the formula I may be those compounds which contain a primary, secondary or tertiary alcoholic group in the molecule. The alkyl radical may be straight-chained or branched and is derived from a corresponding alcohol, for example, octyl alcohol, isononyl alcohol, lauryl alcohol, isotridecyl alcohol, oleyl alcohol, stearyl alcohol; moreover, there may be mentioned mixtures of these alcohols, especially those which are formed in the hydrogenation of natural fatty acids and/or their esters, for example, tallow fat alcohols, palm oil alcohols and coconut oil alcohols. Further alcohols of which the radical $R^1$ may be derived are those which are obtained in technical processes, for example, according to the Ziegler process (ethylene synthesis process) which yields saturated primary alcohols having a straight carbon chain of up to 24 carbon atoms, and according to the various oxo processes which produce more or less branched alcohols. Besides, there may be mentioned aromatic hydroxy compounds, such as phenol, naphthols, 2,4,6-tritertiary butyl-phenol, 4-i-nonylphenol, 4-i-octylphenol, 4-i-propylphenol, cresol, xylene- and 4-i-dodecylphenol.

The oxalkylene group

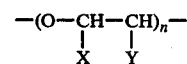

is derived preferably from ethylene or propylene oxide and is introduced by the reaction of the above-mentioned alcohols and aromatic hydroxy compounds with ethylene- and/or propylene oxide. In this process there may also be used mixtures of ethylene oxide and propylene oxide, or the reaction may be effected first with ethylene oxide and then with propylene oxide.

The novel quaternary ammonium compounds show surface-active properties which are interesting in industry and are suitable especially as hair care compositions. They are easily miscible with water and/or ethyl alcohol in all mixing ratios. Those products which show a higher degree of oxethylation (about 10 to 20 units of EO) yield clear solutions, whereas the products having a lower oxethyl content (up to 8 units of EO) are easily dispersible and give a turbid solution. However, they are equally suitable as hair care compositions in either case.

Thus, liquid or pasty hair care compositions with a good fastness to storage may be prepared by simply mixing them with water. An undesired excess amount of quaternary ether amines can be removed from the hair without difficulty with water, and the good distribution ensures also good wet combing properties of the hair thus treated. Also the dry hair still shows satisfactory combing properties.

Besides, the liquid formulations of the quaternary etheramines show only a very slight foaming effect. This is a particular advantage when filling off the ready hair care composition by means of automatic dosing units; in this case, an amount of liquid hair care compositions which is considerably larger can be filled off in the same time unit than it is possible in the case of a foaming aqueous cetyltrimethyl ammonium bromide solution. Also the foam formation which occurs when using, for example, aqueous cetyltrimethyl ammonium chloride, which adversely affects the dressing properties of the hair, is not found when applying aqueous quaternary etheramine solutions in accordance with the present invention.

The following Examples further illustrate the preparation of the novel quaternary ammonium compounds according to the present invention. Unless otherwise stated, all quantitative data are related to the weight.

EXAMPLE 1

The solution of 150 parts of a secondary etheramine, molecular weight 2121, which is obtained by the aminolysis of an oleyl alcohol reacted with 15 moles of ethylene oxide, is introduced into 150 parts of toluene in reaction flask provided with a dropping funnel, stirrer and thermometer. After having added 40 parts of sodium carbonate, 9.8 parts of dimethylsulfate are added dropwise, while stirring, at 60° C within 15 minutes. After stirring for 2 hours at 60° C the reaction mixture is filtered, and 9.8 parts of dimethylsulfate are again added dropwise to the filtrate at 60° C within 15 minutes. After having stirred the mixture once again for 2 hours at 60° C, the toluene is distilled off. A wax-like product which is clearly soluble in water is obtained in a yield of 98%, which corresponds to the following formula, as can be seen by the analytical data:

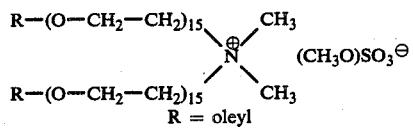

The content of nitrogen showing an alkaline reaction in the starting compound was 0.66%; in the final product it was reduced to 0%, so that a complete quaternization was reached in this case.

EXAMPLE 2

200 Parts of a secondary etheramine of a molecular weight of 854, which is obtained by the aminolysis of a coconut oil alcohol reacted with 5 moles of ethylene oxide, 250 parts of dimethylformamide, 80 parts of sodium hydrogenocarbonate and 33.2 parts of benzylchloride are stirred in a reaction flask provided with stirrer and dropping funnel for 24 hours at 80° C. After filtration and elimination of the dimethylformamide by distillation, an amine is obtained which is secondary to less than 1% and tertiary to more than 99%. The reaction of this product with 32 parts of dimethylsulfate at 60° C and while stirring for 2 hours yields a quaternary ammonium compound which is clearly soluble in water in a yield of 99%, whose content of nitrogen showing an alkaline reaction is 0% and which corresponds to the following formula:

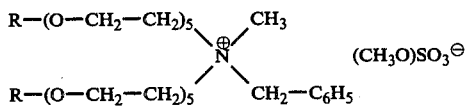

The content of nitrogen showing an alkaline reaction in the starting compound was 1.64%; in the final product it was 0%. This final value was also found in all following Examples.

EXAMPLE 3

400 Parts of a secondary etheramine, molecular weight 787, which is obtained by the aminolysis of a straight-chain $C_{20/22}$-alcohol oxethylated with 2 moles of alkylene oxide, are heated with 30.3 parts of sodium hydroxide and 40 parts of water in a laboratory autoclave having a capacity of 2 liters at a temperature in the range of from 70 to 80° C, in which process methylchloride is pressed on the mixture up to a pressure of 5 kp/cm². When no methylchloride is absorbed any more by the reaction mixture, the latter is aired and the product is filled off. The degree of quaternization is 93%, 1% is free amine, 6% are ammonium hydrochloride. The product can be emulsified in water; its 1% aqueous solution shows a pH value of from 4 to 5.

The content of nitrogen showing an alkaline reaction in the starting compound is 1.78%.

EXAMPLE 4

As has been described in Example 1, 100 parts of a secondary etheramine, molecular weight 1209, which is obtained by the aminolysis of a tributylphenol oxethylated with 8 moles of ethylene oxide, are quaternized in 100 parts of toluene, while adding 40 parts of sodium carbonate, using twice 11.4 parts of dimethylsulfate each. The quaternary ammonium salt of the formula

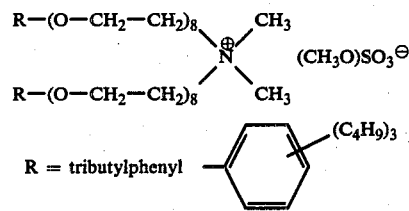

is obtained in a yield of 98%; the content of nitrogen showing an alkaline reaction in the starting compound is 1.16%.

EXAMPLE 5

As has been described in Example 1, 100 parts of a secondary etheramine, molecular weight 952, which is obtained by the aminolysis of a straight-chain $C_{20/22}$ alcohol reacted with 1 mole each of ethylene oxide and propylene oxide, are quaternized in 100 parts of toluene, while adding 40 parts of sodium carbonate, using twice 14.5 parts of dimethylsulfate each.

The content of nitrogen showing an alkaline reaction in the starting compound is 1.47%.

EXAMPLE 6

As has been described in Example 1, 100 parts of a secondary etheramine, molecular weight 615, which is obtained by the aminolysis of a stearyl alcohol reacted with 1 mol of ethylene oxide, are quaternized in 100 parts of toluene, while adding 40 parts of sodium carbonate, using twice 27.5 parts of diethyl sulfate each. A product which does not contain any nitrogen showing an alkaline reaction and which corresponds to the formula

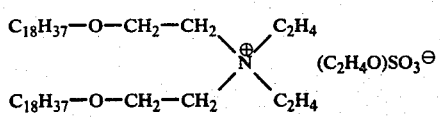

is obtained in a yield of 98%.

The content of nitrogen showing an alkaline reaction in the starting compound is 2.27%.

EXAMPLE 7

200 Parts of a secondary etheramine, molecular weight 952, which is obtained by the aminolysis of a straight-chain $C_{20/22}$-alcohol reacted with 1 mole each of ethylene oxide and propylene oxide, are quaternized, as has been described in Example 3, with 8.4 parts of sodium hydroxide and 16.8 parts of water, while using methylchloride.

A product of the formula

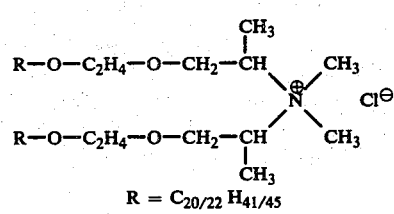

$$R = C_{20/22} H_{41/45}$$

is obtained in a yield of 99%. The degree of quaternization is 92%.

The content of nitrogen showing an alkaline reaction in the starting compound is 1.47%.

In a manner analogous to that of Examples 1 through 7, there are also prepared the novel quaternary ammonium compounds specified in the following Table.

The following Table illustrates the foaming property, measured according to the method of DIN 53 902, of cetyltrimethyl ammonium chloride, cetyltrimethyl ammonium bromide, stearylpentaoxethyl ammonium chloride and a quaternary etheramine compound according to the present invention, measured at 20° C after 25 strokes in a water of a hardness of 20° dH (German hardness) and a concentration of the active ingredient of 0.1%.

Cetyltrimethyl ammonium chloride: 740 cm$^3$
cetyltrimethyl ammonium bromide:
stearylpentaoxethyl ammonium chloride: 490 cm$^3$
quaternary etheramine compound of the constitution:
di(decaoxethyloleyl)-dimethyl ammonium chloride: 40 cm$^3$ The following Application Examples illustrate the various methods of using the quaternary etheramines for the preparation of cationic hair care compositions.

The quantitative data and the percentages in the Examples are related to the weight.

EXAMPLE 8

Clear hair rinsing composition of low viscosity

1% of di(pentadecaoxethyloleyl)-dimethyl ammonium chloride ad 100% of water

EXAMPLE 9

Clear liquid hair rinsing composition of high viscosity 1.5% of di(decaoxethyloleyl)-dimethyl ammonium chloride 1.0% of hydroxyethyl cellulose
0.3% of perfume oil
ad 100% of water

EXAMPLE 10

Liquid hair setting lotion

| | | | | | content of nitrogen showing an alkaline reaction in the starting compound |
|---|---|---|---|---|---|
| $R^1$ | n | $R^2$ | $R^3$ | $A^\ominus$ | |
| $(C_4H_9)_3$—$C_6H_2$ | 2 | $CH_3$ | $CH_3$ | $(CH_3O)SO_3$ | 1.79 |
| " | 4 | $CH_3$ | $CH_3$ | " | 1.54 |
| " | 8 | $CH_3$ | $CH_3$ | " | 1.16 |
| n-$C_9H_{19}$—$C_6H_4$ | 5 | $CH_3$ | $CH_3$ | " | 1.64 |
| " | 10 | $CH_3$ | $CH_3$ | " | 0.97 |
| cyclohexyl | 6 | $C_2H_4$ | $CH_3$ | $(C_2H_4O)SO_3$ | 1.72 |
| $C_{8/10}$ (43% of $C_8$; 55% of $C_{10}$) | 2 | $CH_3$ | $C_2H_4$ | $(CH_3O)SO_3$ | 2.84 |
| " | 10 | $CH_3$ | $CH_3$ | " | 1.17 |
| $C_{12/14}$ (54% of $C_{12}$; 44% of $C_{14}$) | 3 | $CH_3$ | $CH_3$ | Cl | 2.17 |
| $C_{12/14}$ (33% of $C_{12}$; 64% of $C_{14}$) | 3 | $CH_3$ | $CH_3$ | " | 2.15 |
| isotridecyl | 3 | $CH_3$ | $CH_2C_6H_5$ | $(CH_3O)SO_3$ | 2.13 |
| " | 6 | $CH_3$ | $CH_3$ | " | 1.53 |
| " | 10 | $CH_3$ | $CH_3$ | " | 1.09 |
| coconut oil alkyl | 2 | $CH_3$ | $CH_3$ | Cl | 2.38 |
| " | 10 | $CH_3$ | $CH_3$ | " | 0.99 |
| " | 20 | $CH_3$ | $CH_3$ | " | 0.67 |
| tallow fat alkyl | 5 | $CH_3$ | $CH_3$ | " | 2.25 |
| " | 8 | $CH_3$ | $CH_3$ | " | 1.22 |
| " | 15 | $CH_3$ | $CH_3$ | " | 0.70 |
| oleyl | 2 | $CH_3$ | $CH_3$ | " | 2.01 |
| " | 8 | $CH_3$ | $CH_3$ | " | 1.12 |
| " | 10 | $CH_3$ | $CH_3$ | " | 0.97 |
| " | 12 | $CH_3$ | $CH_3$ | " | 0.85 |
| " | 15 | $CH_3$ | $CH_3$ | " | 0.66 |

The content of nitrogen showing an alkaline reaction in the final product was reduced to 0% in all cases, so that a complete quaternization has been reached.

3.5% of vinylpyrrolidone-vinylacetate copolymer in the ratio of 60:40
0.2% of isoadipate 0.3% of perfume oil
45% of isopropyl alcohol
0.2% of di(pentadecaoxethyloleyl)-dimethyl-ammonium-methyl-sulfate
ad 100% of water

EXAMPLE 11

Hair lotion 0.2% of di(dodecaoxethyloleyl)-dimethyl-ammonium-methyl-sulfate 30% of ethyl alcohol
0.4% of isoadepate
0.2% of perfume oil
ad 100% of water

EXAMPLE 12

Shampoo 1.4% of di(decaoxethyloleyl)-dimethyl-ammonium-ethyl-sulfate
15% of lauryldiglycol-ethersulfate-sodium salt
3% of coconut oil acid-diethanolamide
0.3% of perfume oil
1.2% of sodium chloride
0.1% of formalin
ad 100% of water

EXAMPLE 13

Hair rinsing composition in emulsion form

2% of di(pentadecaoxethylstearyl)-dimethyl-ammonium-methyl-sulfate
3% of stearyl alcohol + 10 moles of ethylene oxide 2% of triethylene-glycol-distearate
3% of cetyl alcohol
0.1% of perfume oil
ad 100% of water

EXAMPLE 14

Hair rinsing composition in cream form 0.5% of distearyl-dimethyl-ammonium chloride
1% of di(dodecaoxethyloleyl)-dimethyl-ammonium chloride
3% of cetyl/stearyl alcohol + 9 moles of ethylene oxide
4% of cetyl alcohol
0.2% of perfume oil
ad 0.2100% of water

EXAMPLE 15

Hairdressing cream 0.2% of di(decaoxethyloleyl)-dimethyl-ammonium chloride 5% of diglycerol sesquioleate
15% of paraffin wax
1% of silicone oil
15% of vaseline
2% of paraffin oil
0.1% of perfume oil
ad 100% of water

EXAMPLE 16

Hair spray 1.5% of polyvinylpryrrolidone/vinylacetate copolymer, ratio of 70:30
0.1% of perfume oil
0.1% of silicone oil
0.2% of di(pentadecaoxethyloleyl)-dimethyl-ammonium chloride
28% of ethyl alcohol
ad 100% of fluorinated hydrocarbons as propellent gas.

We claim:

1. Quaternary ammonium compounds of the formula $$\begin{array}{c} \phantom{R^1-(O-}X\phantom{-}Y \\ \phantom{R^1-(O-}|\phantom{-}| \\ R^1-(O-CH-CH)_n \diagdown \phantom{xxx} R^2 \\ \phantom{xxxxxxxxxxxxxxxx}\overset{\oplus}{N} \phantom{x} A^{\ominus} \\ R^1-(O-CH-CH)_n \diagup \phantom{xxx} R^3 \\ \phantom{R^1-(O-}|\phantom{-}| \\ \phantom{R^1-(O-}X\phantom{-}Y \end{array}$$

in which $R^1$ is saturated or unsaturated alkyl radical of 8 to 24 carbon atoms, a cyclohexyl radical or an aryl radical optionally substituted by alkyl groups, X and Y stand for a hydrogen atom or a methyl radical, however, X and Y not being methyl at the same time, n is an integer of from 1 to 20, $R^2$ and $R^3$ stand for an alkyl radical of 1 to 4 carbon atoms or a benzyl radical, and A represents the methosulfate ion, chloride or bromide.

2. Quaternary ammonium compounds as claimed in claim 1, wherein X and Y represent hydrogen atoms.

3. Quaternary ammonium compounds as claimed in claim 1, wherein $R^2$ and $R^3$ represent methyl or ethyl.

4. Method of use of the quaternary ammonium compounds as claimed in claim 1 as active ingredients in hair care compositions.

5. Hair care compositions which contain quaternary ammonium compounds as claimed in claim 1.

6. Method of use of the quaternary ammonium compounds as claimed in claim 2 as active ingredients in hair care compositions.

7. Hair care compositions which contain quaternary ammonium compounds as claimed in claim 2.

8. Method of use of the quaternary ammonium compound as claimed in claim 3 as active ingredients in hair care compositions.

9. Hair care compositions which contain quaternary ammonium compounds as claimed in claim 3.

* * * * *